(12) United States Patent
Elfakhri et al.

(10) Patent No.: US 11,854,188 B2
(45) Date of Patent: Dec. 26, 2023

(54) MACHINE-IMPLEMENTED ACNE GRADING

(71) Applicant: L'ORÉAL, Paris (FR)

(72) Inventors: Christine Elfakhri, Brooklyn, NY (US); Guive Balooch, New York, NY (US); Florent Valceschini, Jersey City, NJ (US); Dominique Moyal, Paris (FR); Hemant Joshi, San Francisco, CA (US); Yuanjie Li, San Francisco, CA (US); Zhiyuan Song, San Francisco, CA (US)

(73) Assignee: L'OREAL, Paris (FR)

( * ) Notice: Subject to any disclaimer, the term of this patent is extended or adjusted under 35 U.S.C. 154(b) by 524 days.

(21) Appl. No.: 17/083,175

(22) Filed: Oct. 28, 2020

(65) Prior Publication Data
US 2021/0133968 A1    May 6, 2021

Related U.S. Application Data

(60) Provisional application No. 62/928,855, filed on Oct. 31, 2019.

(51) Int. Cl.
| | | |
|---|---|---|
| G06K 9/00 | (2022.01) |
| G06T 7/00 | (2017.01) |
| G16H 15/00 | (2018.01) |
| G16H 50/50 | (2018.01) |
| G16H 50/30 | (2018.01) |
| G16H 70/60 | (2018.01) |
| G16H 30/40 | (2018.01) |
| G16H 30/20 | (2018.01) |
| G16H 20/10 | (2018.01) |
| G06N 20/00 | (2019.01) |
| A61B 5/00 | (2006.01) |
| G16H 50/20 | (2018.01) |
| G06Q 30/0601 | (2023.01) |

(52) U.S. Cl.
CPC ............ *G06T 7/0012* (2013.01); *A61B 5/445* (2013.01); *A61B 5/486* (2013.01); *A61B 5/7267* (2013.01); *A61B 5/742* (2013.01); *G06N 20/00* (2019.01); *G16H 15/00* (2018.01); *G16H 20/10* (2018.01); *G16H 30/20* (2018.01); *G16H 30/40* (2018.01); *G16H 50/20* (2018.01); *G16H 50/30* (2018.01); *G16H 50/50* (2018.01); *G16H 70/60* (2018.01); *A61B 5/0077* (2013.01); *A61B 2576/02* (2013.01); *G06Q 30/0631* (2013.01); *G06T 2207/20081* (2013.01); *G06T 2207/30088* (2013.01)

(58) Field of Classification Search
None
See application file for complete search history.

(56) References Cited

U.S. PATENT DOCUMENTS

2021/0027897 A1* 1/2021 Rasochova .......... A61B 5/0077

FOREIGN PATENT DOCUMENTS

WO    WO-2019148116 A1 *   8/2019   ............ A45D 44/00

* cited by examiner

*Primary Examiner* — Wei Wen Yang
(74) *Attorney, Agent, or Firm* — Oblon, McClelland, Maier & Neustadt, L.L.P.

(57) ABSTRACT

An image is accepted by one or more processing circuits from a user depicting the user's skin. Machine learning models stored in one or more memory circuits are applied to the image to classify acne characteristics. An acne severity grade is provided by the one or more processing circuits and a user interface displays the acne severity grade.

13 Claims, 5 Drawing Sheets

MACHINE-IMPLEMENTED ACNE GRADING

CROSS-REFERENCE TO RELATED APPLICATIONS

The present application claims the benefit of priority to U.S. Provisional Application No. 62/928,855, "MACHINE-IMPLEMENTED ACNE GRADING" filed Oct. 31, 2019, which is incorporated by reference herein in its entirety.

BACKGROUND

*Acne vulgaris*, or simply acne, is a skin disease characterized by, among other things, whiteheads, blackheads, papules, pustules, and nodular cysts. Treatment for acne is widely available and includes both over-the-counter and prescription products. Diagnosing acne and recommending an effective treatment for the kind of acne a particular person suffers from often requires expert diagnoses, such as by a dermatologist. Nevertheless, many people seek treatment from a general practitioner, who may lack the training needed to properly diagnose the severity of the patient's acne and hence a proper treatment. Tools for assisting general practitioners and even general users in arriving at effective treatments for acne are needed.

SUMMARY

An image is accepted by one or more processing circuits from a user depicting the user's skin. Machine learning models stored in one or more memory circuits are applied to the image to classify acne characteristics. An acne severity grade is provided by the one or more processing circuits and a user interface displays the acne severity grade.

Figure 1:
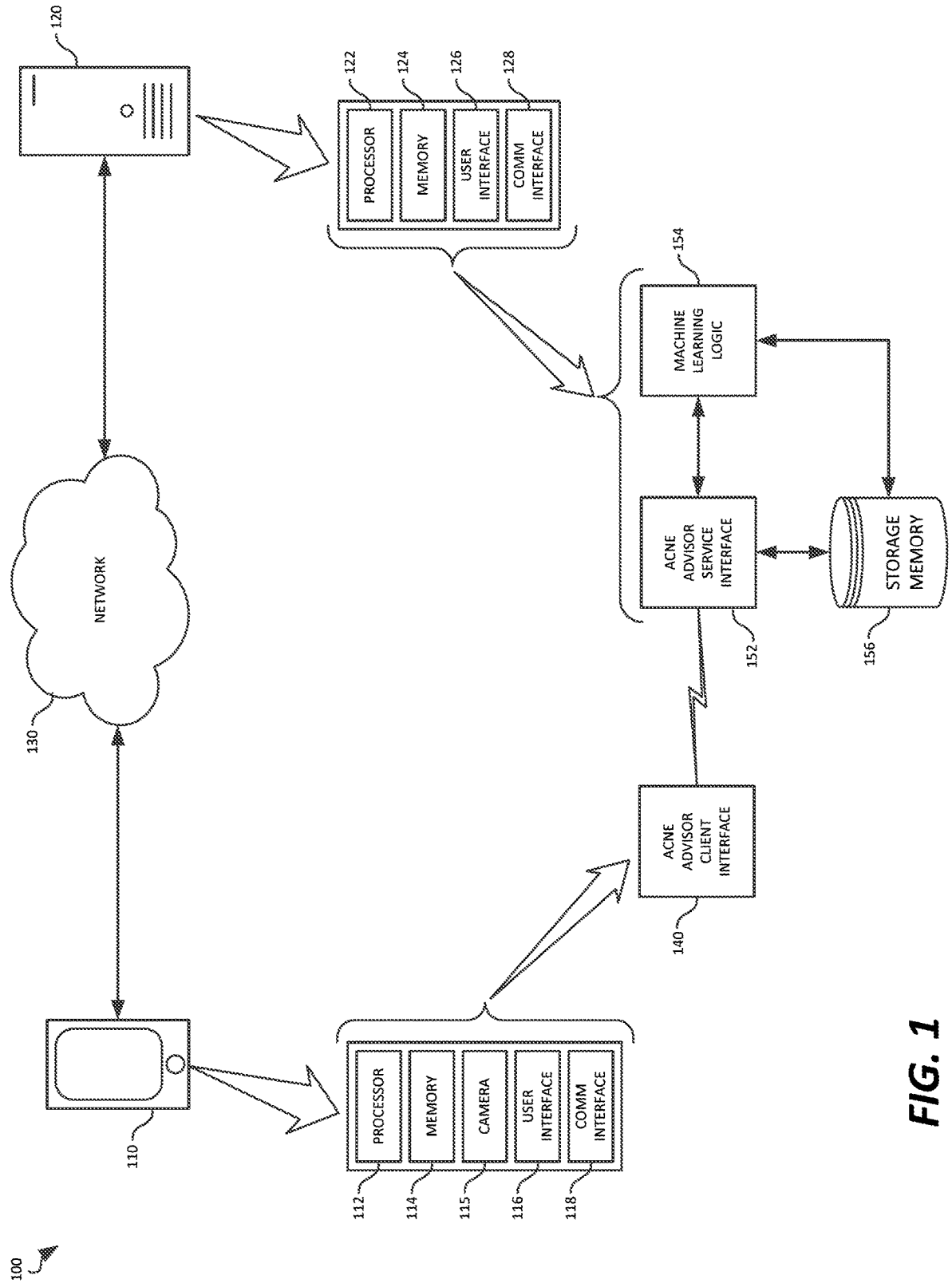
FIG. 1 is a schematic block diagram of an example system configuration by which the present general inventive concept can be embodied.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, the word exemplary is used herein to mean, "serving as an example, instance or illustration." Any embodiment of construction, process, design, technique, etc., designated herein as exemplary is not necessarily to be construed as preferred or advantageous over other such embodiments. Particular quality or fitness of the examples indicated herein as exemplary is neither intended nor should be inferred.

DESCRIPTION

FIG. 1 is a schematic block diagram of an exemplary acne advisor system 100 comprising an acne advisor client platform 110 and an acne advisor service platform 120 communicatively coupled through a network 130. In one embodiment, acne advisor client platform 110 is a smartphone, tablet computer or other mobile computing device, although the present invention is not so limited. As illustrated in FIG. 1, exemplary acne advisor client platform 110 comprises a processor 112, memory 114, a camera 115, a user interface 116 and a communication interface 118 over which an acne advisor client interface 140 may be implemented. Acne advisor client interface 140 provides the primary portal through which a user accesses acne advisor system 100.

In one embodiment of the present invention, acne advisor service platform 120 comprises one or more server computers, each comprising a processor 122, a memory 124, a user interface 126 and a communication interface 128. These resources of acne advisor service platform 120 may be utilized to implement an acne advisor service interface 152, machine learning logic 154 and a storage memory 156. Storage memory 156 represents a sufficient amount of volatile and persistent memory to embody the invention. Storage memory 156 may contain vast amounts of encoded human knowledge as well as space for the private profiles of individual users. Storage memory 156 may further store processor instructions that, when executed by one or more processors 122, perform some task or procedure for embodiments of the invention. Storage memory 156 may further store user models (coefficients, weights, processor instructions, etc.) that are operable with machine learning logic 154 to grade a person's skin on a predetermined acne grading scale. In one embodiment, the acne grading scale is the Global Evaluation Acne (GEA) scale. In that scale, grade zero (0) indicates normal, clear skin with no evidence of acne; grade one (1) indicates that the skin is almost clear—rare non-inflammatory lesions are present, with rare non-inflamed papules (papules must be resolving and may be hyper-pigmented, though not pink-red); grade two (2) indicates that some non-inflammatory lesions are present, with few inflammatory lesions (papules/pustules only, no nodulo-cystic lesions); grade three (3) indicates that non-inflammatory lesions predominate, with multiple inflammatory lesions evident—several to many comedones and papules/pustules and there may or may not be a small nodulo-cystic lesion; grade four (4) indicates inflammatory lesions are more apparent—many comedones and papules/pustules and there may or may not be a few nodulo-cystic lesions; and grade 5 indicates highly inflammatory lesions predominate—variable number of comedones, many papules/pustules and nodulo-cystic lesions. Each of the grades may be associated with remedial action and certain embodiments may prescribe a particular regimen for a user and may track the user's progress under the regimen. As used herein, a regimen is a systematic plan or course of action intended to improve the health and/or beauty of a human user. In the facial health and beauty domain, a regimen might include cleaning the skin with a specific cleanser, applying specific creams, etc.

Exemplary acne advisor service interface 152 provides the infrastructure by which network access to acne advisor services are both facilitated and controlled. Acne advisor client interface 140 and acne advisor service interface 152 communicate via a suitable communication link 145 using the signaling and data transport protocols for which communication interface 118 and communication interface 128 are configured. Acne advisor service interface 156 may implement suitable Internet hosting services as well as authentication and other security mechanisms that allow access only to authorized users and protect the users' private data. Additionally, acne advisor service interface 152 may realize an application programming interface (API) that affords acne advisor client interface 140 communications with, for example, machine learning logic 154. Those having skill in the art will recognize other front-end services that can be used in conjunction with the present invention.

Machine learning logic 154 provides the infrastructure for embodiments of the invention to learn from and make predictions about data without being explicitly programmed to do so. In certain embodiments, machine learning logic 154 implements one or more convolutional neural networks (CNNs), the models for which may be trained using private or open source datasets. Other machine learning techniques may be used in conjunction with the present invention including, but not limited to, decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning and learning classifiers. Additional techniques described in U.S. Pat. Nos. 8,442,321, 9,015,083, 9,536,293, 9,324,022, and U.S. PG Publication No. 2014/0376819 A1, all of which are incorporated herein by reference, may be used with the present invention. In the descriptions that follow, it will be assumed that machine learning logic implements a convolutional neural network, although the present invention is not so limited. Those having skill in artificial intelligence will recognize numerous techniques that can be used in conjunction with the present invention without departing from the spirit and intended scope thereof.

Figure 2:
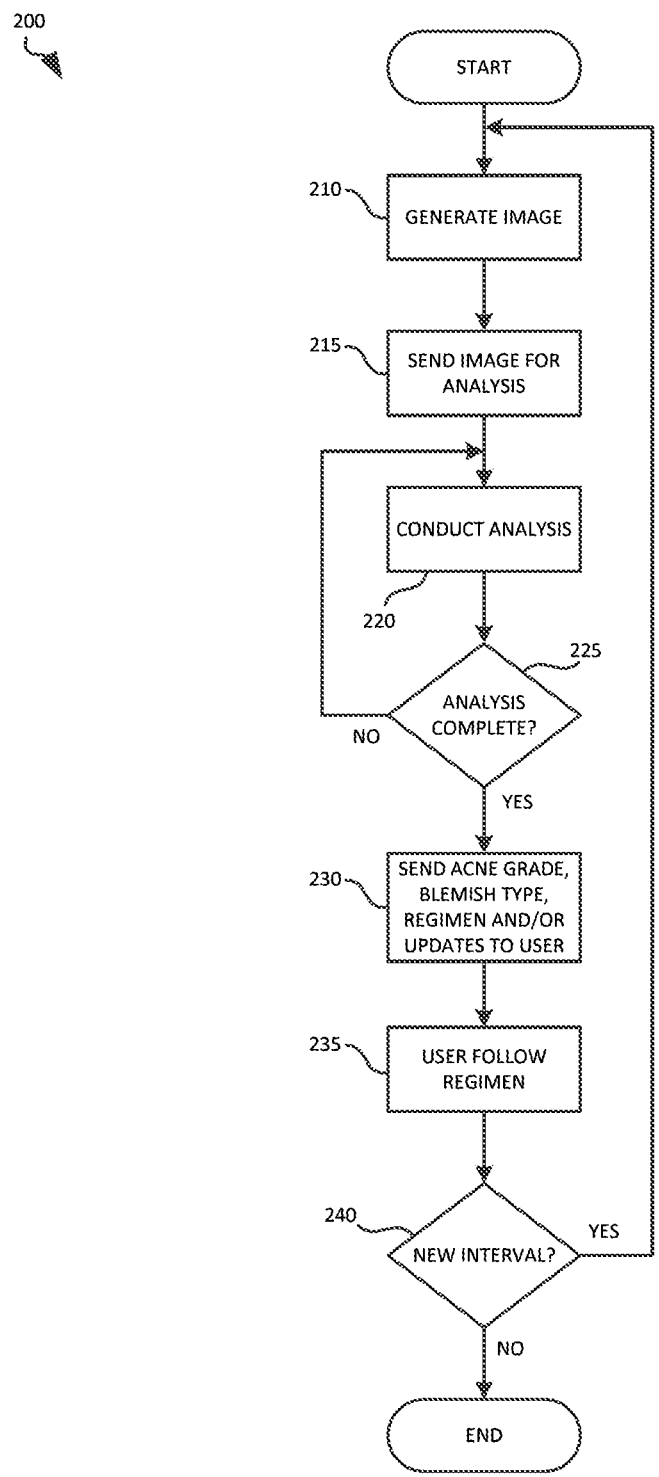
FIG. 2 is a flow diagram of a simple user interaction with an embodiment of the present general inventive concept.

FIG. 2 is a flow diagram by which an example interaction with an embodiment of the invention can be explained. The interaction of FIG. 2 is simple by design and is no way intended to be limiting. The description of FIG. 2 is intended to illustrate functionality of the configuration illustrated in FIG. 1. Further features of the invention, beyond those described with reference to FIG. 2, will be discussed below.

In operation 210, a user may generate an image of his face or other area of skin, such as by camera 116 of acne advisor client platform 110. In operation 215, the user's image is sent to acne advisor service platform 120. This may be achieved by suitable communication protocols shared between acne advisor client platform 110 and acne advisor service platform 120 to realize communication link 145.

In operation 220, image analysis and machine learning are conducted to analyze the user's skin from the images. Machine learning logic 154 may perform analyses that determine a grade of acne from the image of the user's skin. This may be achieved by segmenting the images and classifying features in the segmented regions. Such feature classification may be achieved through models trained by subject matter experts, e.g., dermatologists. For example, machine learning logic 154 may segment an image into different regions that contain features such as bumps and other formations on the skin, areas of discoloration, etc., and then classify those features as lesions of different types, inflamed skin, and so on. In certain embodiments, the classified features are provided to the user as, for example, blemish types. Such blemish types may include inflammatory types (e.g., cysts, nodules, papules, pustules, etc.), non-inflammatory types (e.g., blackheads, whiteheads, etc.) and moderate-to-severe types (e.g., nodules, cysts, etc.), which are identified based on the classified features. Once the features have been classified, machine learning logic 154 may be trained to grade the acne, such as through the GEA scale described above.

In operation 225, it is determined whether the analysis is complete and, responsive to a positive determination thereof, process 200 may transition to operation 230, whereby acne advisor service interface 152 sends the acne grade (with or without the aforementioned blemish types), a recommended regimen or updates to a regimen to acne advisor client interface 140 in operation 230. Example regimens include those that breakdown whiteheads and blackheads (benzoyl peroxide to fight bacteria, salicylic acid to remove dead skin, sulfur, resorcinol). Other example regimens include washing the face with lukewarm water and soap twice daily, washing the whole body every 2 days, reducing stress, eating a healthful, balanced diet, staying hydrated, avoiding over-washing or irritating the skin, limiting exposure to the sun, always wearing sunscreen when outdoors. Other regimens may be recommended by embodiments of the present invention according to either or both of acne grade and blemish type.

The user may follow the regimen as indicated in operation 235 and, in operation 240, it is determined whether a new interval has commenced. If so, process 200 reiterates from operation 210. Acne advisor client interface 140 may access calendars and timers (as well as GPS) onboard acne advisor client platform 110 as well as access to network-accessible calendars on network 130. Accordingly, once a week, say, acne advisor client interface 140 may remind the user to take a picture of his skin, i.e., remind him of the new interval. Over time, acne advisor system 100 can determine from the images taken at each interval whether the recommended regimen is working and, if not, acne advisor system 100 may revise the regimen, e.g., change a product, recommend further lifestyle changes, make a dermatologist's appointment, etc. In certain embodiments, time-series analyses may be conducted on the images taken over several intervals to determine, for example, the rate of change of the dimensions, shape and other characteristics of a suspected acne lesion. Such time-series analyses may be used to assess the efficiency and efficacy of a particular regimen.

Figure 3:
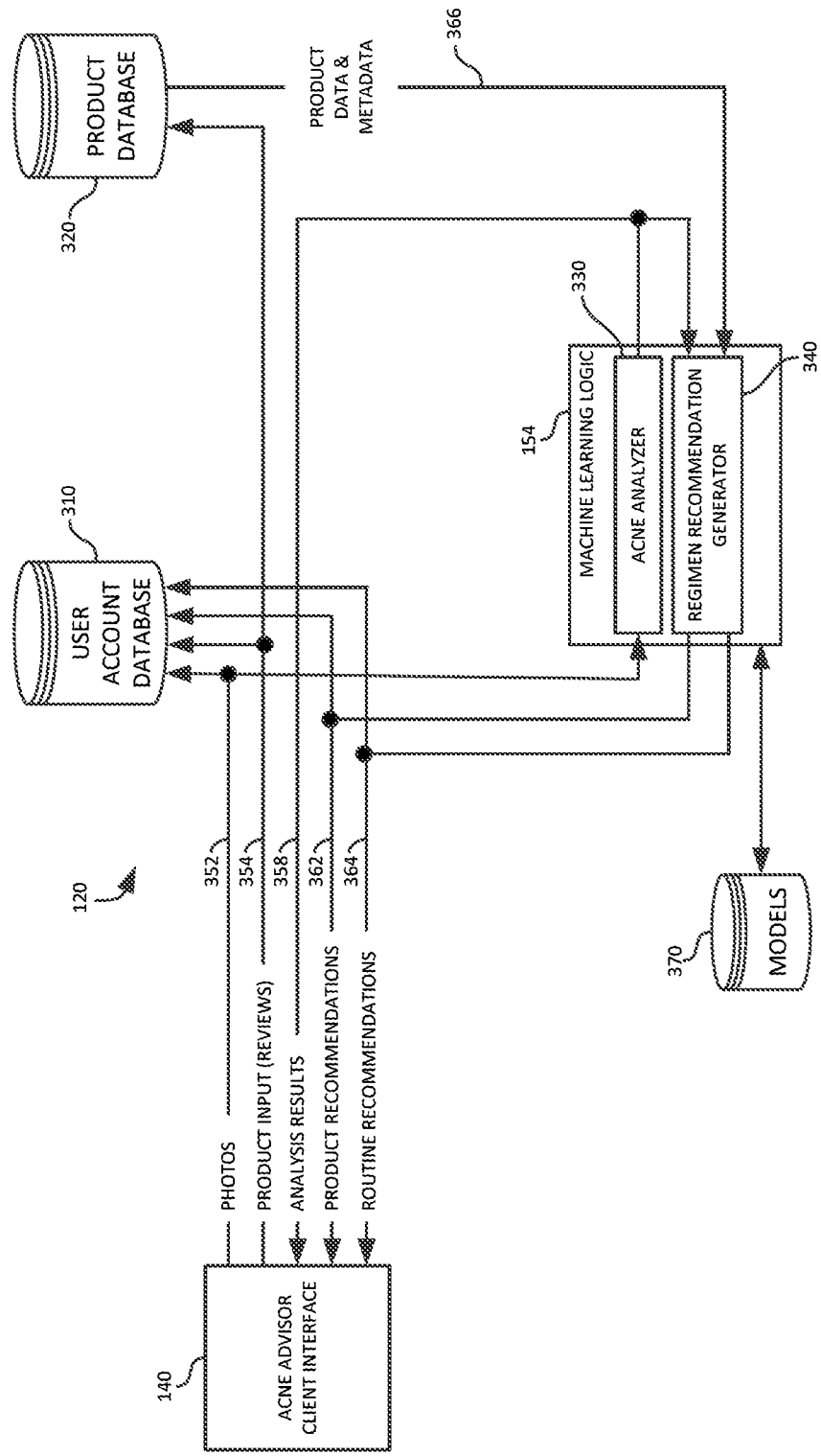
FIG. 3 is a schematic block diagram of example data flow of an embodiment of the present general inventive concept.

FIG. 3 is a diagram of data flow between an exemplary acne advisor client interface 140 and services of acne advisor service platform 120. It should be noted that, in FIG. 3, acne advisor service interface 152 has been omitted to avoid unnecessary congestion in the figure. However, those having skill in the relevant arts will recognize the operation of an acne advisor service interface 152 to control and facilitate the data flow depicted in FIG. 3.

As illustrated in FIG. 3, machine learning logic 154 may comprise a skin analyzer 330 and a regimen recommendation generator 340 and may be communicatively coupled to a user account database 310 and a product database 320. Machine learning logic 154 may train and utilize machine learning models 370 to recommend regimens and to track the progress of the user under the regimen. As those skilled in machine learning will attest, training may involve selecting a set of features, e.g., redness, inflamed lesions, papules/pustules, comedones, etc., and assigning labels to image data that reflects the presence or prominence of those features. The assigning of labels may be performed by a subject matter expert such as a dermatologist. Taking the assigned labels as ground truth, machine learning logic 154 may configure models 370 to predict the degree to which the features are present in a test image, which may change over time. The present invention is not limited to a particular model representation, which may include binary models, multiclass classification models, regression models, etc.

Exemplary user account database 310 contains the data of all users of acne advisor system 100 in a secure manner. This includes user profile data, current and past user photos 352 for each user, current and past skin analyses 358 for each user, current and past product recommendations 362 and current and past routine recommendations 364 for each user.

Exemplary product database 320 contains the data of different products that can be used in a regimen. Product database 320 may contain records reflecting the product names, active and inactive ingredients, label information, recommended uses, and so on. In certain embodiments, as illustrated as product input 354, the user (and other users of acne advisor system 100) may provide feedback on different products and may enter products not already in product database 320. Past and present product input 354 may be stored in association with the user's account. The present invention is not limited to particular products that can be entered in product database 320.

Acne analyzer 330 is constructed or is otherwise configured to classify acne from imagery of a user's face or other region of skin using machine learning techniques and models 370. In certain embodiments, photographic images 352 of a user's face or other areas of skin are provided to skin analyzer 330 for analysis. Skin analyzer 330 may implement image preprocessing mechanisms that include cropping, rotating, registering and filtering input images prior to analysis. After any such preprocessing, skin analyzer 330 may apply models 370 to the input image 352 to locate, identify and classify acne characteristics of the user's skin.

Regimen recommendation generator 340 may operate on analysis results 358 obtained from skin analyzer 330 towards prescribing a regimen to the user. Models 370 may be trained to predict what products and routines (treatment, cosmetic and lifestyle recommendations, etc.) would be effective in meeting the user's goal with regard to acne identified in the skin analysis. Regimen recommendation generator 340 may format the analysis results 358 of skin analyzer 330 as a query into, for example, product database 320 based on knowledge encoded on models 370. In response, product database 320 may return product data and metadata 366, and product recommendations 362 and routine recommendations 364 may be provided to acne advisor client interface 140.

Figure 4:
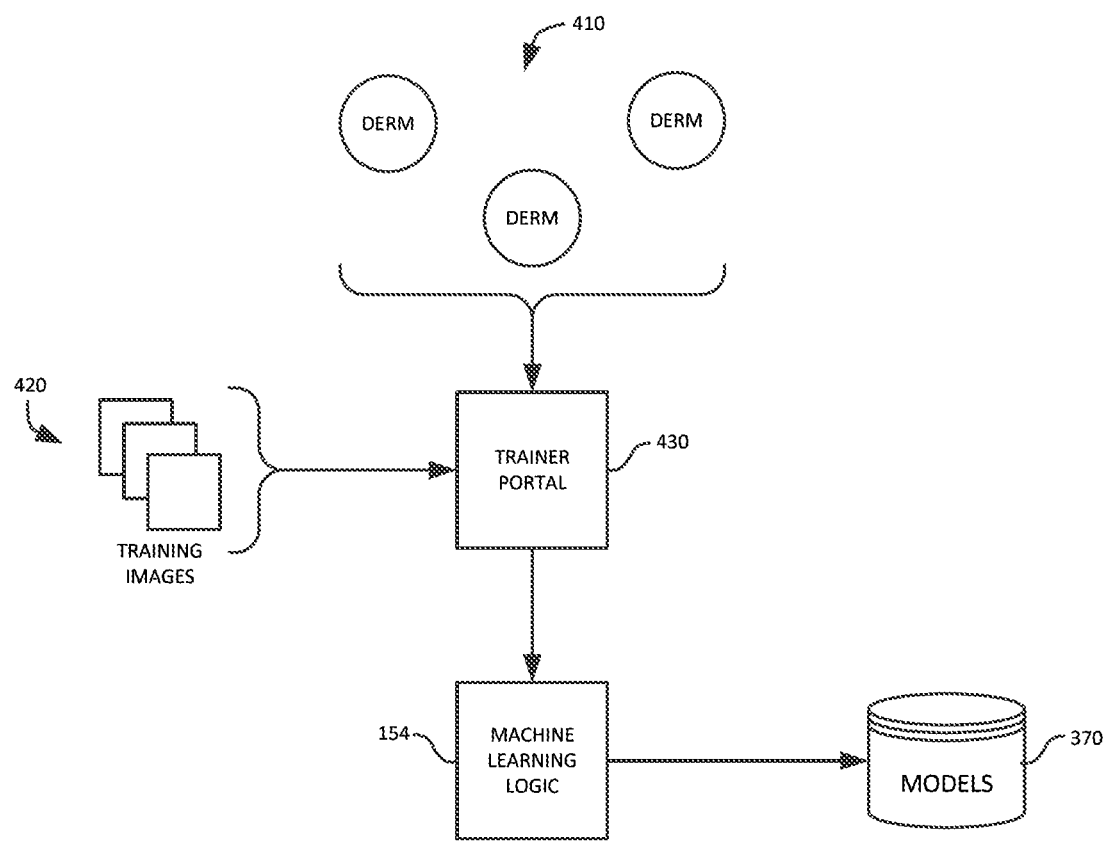
FIG. 4 is a block diagram of dermatologist training of machine learning models according to an embodiment of the present general inventive concept.

As indicated above, training of models 370 may be achieved by labeling of image data by an expert. FIG. 4 is a diagram of an embodiment of the invention illustrating such training. During training, experts, in this case dermatologists 410 are presented a set of training images 420 through a training portal 430. Dermatologists 410 interact with training portal 430 to characterize acne characteristics presented in the images and to grade acne based on the acne characteristics. These data may be used to train models 370 in accordance with which machine learning logic 154 subsequently classifies acne features and grades a user's acne without human intervention.

Figure 5:
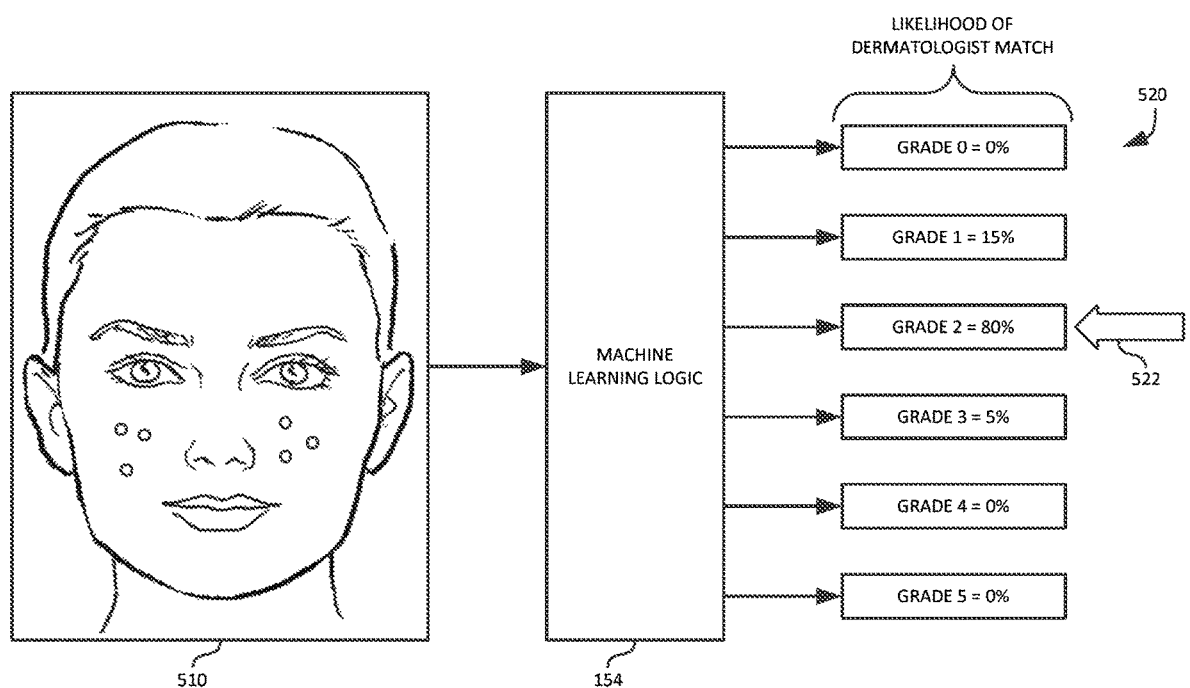
FIG. 5 is a diagram illustrating a test operation in accordance with the dermatologist machine learning model training.

FIG. 5 illustrates an example test operation in accordance with the training discussed above. A test image 710, i.e., a user's own image, may be presented to machine learning logic 154, which analyzes the image per the models trained by the subject matter experts. As illustrated in the figure, machine learning logic 154 estimates that 80% of the expert dermatologists would give the user's acne a grade 2, as indicated at 522. Accordingly, machine learning logic 154 may recommend a regimen, (e.g., a cream specially formulated for grade 2 acne and recommended application instructions), based on the GEA acne grade. In another embodiment, machine learning logic 154 may provide one or more blemish types corresponding with a highest probability of agreement by subject matter experts.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be, for example, but is not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a solid state disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a phase change memory storage device, or any suitable combination of the foregoing. In the context of this document, a computer readable storage medium may be any tangible medium that can contain, or store a program for use by or in connection with an instruction execution system, apparatus, or device.

Computer program code for carrying out operations for aspects of the present invention may be written in any combination of one or more programming languages, e.g., an object oriented programming language such as Java, Smalltalk, C++ or the like, or a conventional procedural programming language, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). It is to be understood that the software for the computer systems of the present invention embodiments may be developed by one of ordinary skill in the computer arts based on the functional descriptions contained in the specification and flow charts illustrated in the drawings. Further, any references herein of software performing various functions generally refer to computer systems or processors performing those functions under software control.

The computer systems of the present invention embodiments may alternatively be implemented by any type of hardware and/or other processing circuitry. The various functions of the computer systems may be distributed in any manner among any quantity of software modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.).

The foregoing examples are illustrative of certain functionality of embodiments of the invention and are not intended to be limiting. Indeed, other functionality and other possible use cases will be apparent to the skilled artisan upon review of this disclosure.

The invention claimed is:

1. A system comprising:
one or more memory circuits configured to store machine learning models;
one or more processing circuits configured to:
accept at least one image from a user depicting the user's skin;
apply the machine learning models to the image to classify acne characteristics; and
provide an indication of the classified acne characteristics; and
a user interface configured to display the provided indication of the classified acne characteristics,
wherein the one or more processing circuits is further configured to generate a regimen recommendation based on the classified acne characteristics and the user interface is further configured to display the generated regimen recommendation,
wherein the one or more processing circuits is further configured to:
accept another image from the user depicting the user's skin;
apply the machine learning models to the other image to classify the acne characteristics; and
update the regimen recommendation to the user based on the classified acne characteristics of the other image.

2. The system of claim 1, wherein the indication of the classified acne characteristics is an acne severity grade that has a highest probability of being diagnosed by a human dermatologist.

3. The system of claim 2, wherein the acne severity grade complies with the Global Evaluation Acne scale.

4. The system of claim 1, wherein the indication of the classified acne characteristics is one or more acne blemish types that has a highest probability of being diagnosed by a human dermatologist.

5. The system of claim 4, wherein the acne blemish types include inflammatory types, non-inflammatory types and moderate-to-severe types.

6. The system of claim 1, wherein the one or more processing circuits are physically separated into a client platform and a service platform communicatively coupled through a communication network.

7. A method comprising:
accepting at least one image from a user depicting the user's skin;
applying machine learning models to the image to classify acne characteristics;
determining, by one or more processors, an indication of the classified acne characteristics;
displaying the indication of the classified acne characteristics to the user;
generating a regimen recommendation based on the classified acne characteristics; and
displaying the generated regimen recommendation;
accepting another image from the user depicting the user's skin;
applying the machine learning models to the other image to classify acne characteristics; and
updating the regimen recommendation to the user based on the classified acne characteristics of the other image.

8. The method of claim 7 further comprising:
accepting input from a plurality of experts that classify the acne characteristics from training images provided thereto; and
training the models using the accepted input.

9. A tangible, non-transitory computer-readable medium having encoded thereon processor instructions that, when executed by one or more processors, cause the processors to:
accept at least one image from a user depicting the user's skin;
apply machine learning models stored in memory circuitry to the image to classify acne characteristics; and
provide an indication of the classified acne characteristics;
display the provided indication of the classified acne characteristics additional processor instructions that cause the one or more processors to:
generate a regimen recommendation based on the classified acne characteristics;
display the generated regimen recommendation;
additional processor instructions that cause the one or more processors to:
accept another image from the user depicting the user's skin;
apply the machine learning models to the other image to classify the acne characteristics; and
update the regimen recommendation to the user based on the classified acne characteristics of the other image.

10. The computer-readable medium of claim 9, wherein the indication of the classified acne characteristics is an acne severity grade that has a highest probability of being diagnosed by a human dermatologist.

11. The computer-readable medium of claim 10, wherein the acne severity grade complies with the Global Evaluation Acne scale.

12. The computer-readable medium of claim 9, wherein the indication of the classified acne characteristics is one or more acne blemish types that has a highest probability of being diagnosed by a human dermatologist.

13. The computer-readable medium of claim 12, wherein the acne blemish types include inflammatory types, non-inflammatory types and moderate-to-severe types.

* * * * *